(12) United States Patent
Kumagai

(10) Patent No.: US 7,672,819 B2
(45) Date of Patent: Mar. 2, 2010

(54) SPOT WELD FRACTURE ANALYSIS METHOD, PROGRAM THEREFOR, AND ANALYSIS APPARATUS THEREOF

(75) Inventor: Koushi Kumagai, Nagoya (JP)

(73) Assignee: Toyota Jidosha Kabushiki Kaisha, Toyota-shi (TW)

( * ) Notice: Subject to any disclaimer, the term of this patent is extended or adjusted under 35 U.S.C. 154(b) by 701 days.

(21) Appl. No.: 11/580,163

(22) Filed: Oct. 13, 2006

(65) Prior Publication Data

US 2007/0090165 A1  Apr. 26, 2007

(30) Foreign Application Priority Data

Oct. 20, 2005  (JP) .............................. 2005-305717

(51) Int. Cl.
*G06G 7/28* (2006.01)
*B23K 31/12* (2006.01)

(52) U.S. Cl. .................. 703/6; 703/7; 703/8; 228/103; 228/101

(58) Field of Classification Search .................. 703/6–8; 228/101, 103
See application file for complete search history.

(56) References Cited

U.S. PATENT DOCUMENTS

| 6,627,841 | B2 * | 9/2003 | Chen et al. .................. 219/110 |
| 6,789,051 | B1 * | 9/2004 | Chen et al. ....................... 703/2 |
| 2008/0312882 | A1 * | 12/2008 | Kumagai ....................... 703/1 |

FOREIGN PATENT DOCUMENTS

JP  2003-149130  5/2003

WO  WO 2004099761 A1 * 11/2004

OTHER PUBLICATIONS

Finite element modeling of friction stir welding—thermal and thermomechanical analysis; C. M. Chen and R. Kovacevic International Journal of Machine Tools and Manufacture vol. 43, Issue 13, Oct. 2003, pp. 1319-1326.*

Residual stress analysis of laser spot welding of steel sheets; P. Martinson et al Materials & Design vol. 30, Issue 9, Oct. 2009, pp. 3351-3359.*

(Continued)

*Primary Examiner*—Kamini S Shah
*Assistant Examiner*—Akash Saxena
(74) *Attorney, Agent, or Firm*—Oblon, Spivak, McClelland, Maier & Neustadt, L.L.P.

(57) ABSTRACT

A spot weld fracture analysis method for a spot weld portion of three or more mutually superimposed plates that are spot-welded at a common welding point comprises an analysis step of executing an analysis by using a finite element model in which each plate is modeled by shell elements, and the shell elements corresponding to a spot weld point position of each plate are individually interconnected via beam elements, and a prediction step of finding an element force of a beam element that acts on a shell element relevant to a middle plate from a difference between the element forces of two beam elements connected to the shell element on a basis of the analysis result, and predicting a possibility of fracture of a spot weld between the middle plate and an adjacent plate by using the difference element force found from the difference.

4 Claims, 9 Drawing Sheets

OTHER PUBLICATIONS

Resistance spot welding simulation: a general finite element formulation of electrothermal contact conditions E. Feulvarch et al Journal of Materials Processing Technology vols. 153-154, Nov. 10, 2004, pp. 436-441.*

S.-H. Lin, et al. "Modeling and Testing of Spot Welds under Dynamic Impact Loading Conditions", SAE Paper 2002-01-0149/, SAE 2002 World Congress, Detroit, Michigan, Mar. 4-7, 2002, 9 pages.*

Chelliah Madasamy, et al., "Methodology for Testing of Spot-Welded Steel Connections Under Static and Impact Loadings", SAE Paper 2003-01-0608/, SAE 2003 World Congress, Detroit, Michigan, Mar. 3-6, 2003, 10 pages.*

Chelliah Madasamy, et al., "An Investigation of Spot-Welded Steel Connections Using a DOE Approach", SAE Paper AW 2003-01-0612/, SAE 2003 World Congress, Detroit, Michigan, Mar. 3-6, 2003, 11 pages.*

Chelliah Madasamy, et al., "Finite Element Modeling of Spot Weld Connections in Crash Applications", SAE Paper 2004o01-0691, SAE 2004 World Congress, Detroit, Michigan, Mar. 8-11, 2004, 10 pages.*

S.-H. Lin, et al., A General Failure Criterion for Spot Welds with Consideration of Plastic Anisotropy and Separation Speed, SAE Paper 2003-01-0611/, SAE 2003 World Congress, Detroit, Michigan Mar. 3-6, 2003, 9 pages.

Chelliah Madasamy, et al., "An Investigation of Spot-Welded Steel Connections Using a DOE Approach", SAE Paper 2003-01-0612/, SAE 2003 World Congress, Detroit, Michigan, Mar. 3-6, 2003, 11 pages.

Chelliah Madasamy, et al., "Finite Element Modeling of Spot Weld Connections in Crash Applications", SAE Paper 2003-01-0691/, SAE 2004 World Congress, Detroit, Michigan, Mar. 8-11, 2004, 10 pages.

Shinichiro Yoda, et al., "Development of a Method to Predict the Rupture of Spot Welds in Vehicle Crash Analysis", SAE Paper 2003-01-0533/, SAE 2006 World Congress, Detroit, Michigan, Apr. 3-6, 2006, 9 pages.

Chelliah Madasamy, et al., "Finite Element Modeling of Spot Weld Connections in Crash Applications", SAE Paper 2004-01-0691, SAE 2004 World Congress, Detroit, Michigan, Mar. 8-11, 2004, 10 pages.

Shinichiro Yoda, et al., "Development of a Method to Predict the Rupture of Spot Welds in Vehicle Crash Analysis", SAE Paper 2006-01-0533, SAE 2006 World Congress, Detroit, Michigan, Apr. 3-6, 2006, 9 pages.

* cited by examiner $F(t_1, M_1, F_1, \varepsilon_1, \dot{\varepsilon}_1, C_1,$  ...) > $F_{cr}$ $F(t_2, M_1-M_2, F_1-F_2, \varepsilon_2, \dot{\varepsilon}_2, C_2,$  ...) > $F_{cr}$ $F(t_2, M_2-M_1, F_2-F_1, \varepsilon_2, \dot{\varepsilon}_2, C_2,$  ...) > $F_{cr}$ $F(t_3, M_2, F_2, \varepsilon_3, \dot{\varepsilon}_3, C_3,$  ...) > $F_{cr}$

DIFFERENCE ELEMENT FORCES F'

(DETERMINATION ON 1ST GROUP SIDE) — BEAM 1, t1, t2

(DETERMINATION ON 2ND GROUP SIDE) — BEAM 2, t2, t3

SPOT WELD FRACTURE ANALYSIS METHOD, PROGRAM THEREFOR, AND ANALYSIS APPARATUS THEREOF

INCORPORATION BY REFERENCE

The disclosure of Japanese Patent Application No. 2005-305717 filed on Oct. 20, 2005, including the specification, drawings and abstract, is incorporated herein by reference in its entirety.

BACKGROUND OF THE INVENTION

1. Field of Invention

The invention relates to a fracture analysis method for a spot weld portion of three or more mutually superimposed plates that are spot-welded at a common welding point and a computer-readable program for executing the method as well as a spot weld fracture analysis apparatus.

2. Description of Related Art

There is a known fatigue life prediction method for a spot-welded structure characterized in that two plates are joined to form a spot-welded structure, and that a finite element analysis-purpose shell model for the spot-welded structure is created, and that using the created purpose shell model, a finite element linear elastic analysis is performed to calculate the share load of a nugget portion at the center of a spot weld portion, and the deflection on the circumference of a circle of a diameter D described with the nugget portion being the center, and the inclination in radial directions, and that, on the basis of the share load, the deflection on the circumference and the inclination in radial directions that have been calculated, the nominal structural stress in the nugget portion is found through the use of a disc bending theory in the theory of elasticity, and that, from the nominal structural stress, a fatigue life of the spot-welded structure is predicted (e.g., see Japanese Patent Application Laid-Open Publication No. 2003-149130).

A spot weld portion of three or more mutually superposed plates that are spot-welded at a common welding point can be modeled, for example, by modeling each plate by shell elements, and connecting the shell elements corresponding to the spot welding point positions of the individual plates via beam elements. Such a finite element model is substantially equal to a mode in which two plates are respectively spot-welded to each other at a time. That is, for example, in the case of three-plate welding, a mode is obtained in which the middle plate is spot-welded separately to the two side plates.

Consequently, in the case where such a finite element model is used, a fracture determination method whose conformity with regard to the spot welding of two plates has been established can be utilized for every group that is made up of two plates.

However, in the case where the fracture analysis method is directly utilized, the fracture analysis on a group does not take into account the element force of the beam element in another group. Therefore, a problem is that the possibility of fracture of the spot weld portion on a middle plate belonging to two groups (i.e., a middle plate that forms groups with two plates (inside and outside plates)) cannot be appropriately analyzed or predicted.

SUMMARY OF THE INVENTION

It is an object of the invention to provide a fracture analysis method for a spot weld portion in which a fracture analysis can be performed at high accuracy with respect to spot weld portions of three or more plates that are spot-welded at a common welding point and a computer-readable program for executing the method as well as a spot weld fracture analysis apparatus.

A first aspect of the invention relates to a spot weld fracture analysis method for a spot weld portion of three or more mutually superimposed plates that are spot-welded at a common welding point. In the spot weld fracture analysis method, each plate is modeled by shell elements; an analysis is executed under a predetermined input load condition by using a finite element model in which shell elements corresponding to a spot weld point position of each plate of the three or more plates are individually interconnected via beam elements; an element force of a beam element that acts on a shell element relevant to a middle plate of the three or more plates is found from a difference between the element forces of two beam elements that are connected to the shell element relevant to the middle plate, on a basis of an analysis result obtained via the analysis; and a possibility of fracture of a spot weld between the middle plate and an adjacent plate is predicted by using the element force found from the difference.

In the spot weld fracture analysis method, in order to predict the possibility of fracture of the spot weld, a given fracture function that, through inputting as parameters at least an element force of a beam element, a strain of a shell element connected to the beam element, and plate thickness information regarding a plate relevant to the shell element, outputs an index value that represents a possibility of fracture on a side of the plate relevant to the shell element is used; the possibility of fracture of the spot weld between the middle plate and the adjacent plate is judged on a basis of an output value of the fracture function relevant to each plate; and the difference element force is input as an element force of the beam element that is one of the parameters, into the fracture function relevant to the middle plate.

The spot weld fracture analysis apparatus includes: a model creation device that models each plate by shell elements; an analysis device that acquires an analysis result of a dynamic structural analysis based on a finite element model in which shell elements corresponding to a spot weld point position of each plate of the three or more plates are individually interconnected via beam elements; and a prediction device that finds an element force of a beam element that acts on a shell element relevant to a middle plate of the three or more plates from a difference between the element forces of two beam elements that are connected to the shell element relevant to the middle plate on a basis of the analysis result, and that predicts a possibility of fracture of a spot weld between the middle plate and an adjacent plate by using the element force found.

According to the aspect of the invention, a spot weld fracture analysis method for a spot weld portion in which a fracture analysis can be performed at high accuracy with respect to spot weld portions of three or more plates that are spot-welded at a common welding point, and a computer-readable program for executing the method, as well as a spot weld fracture analysis apparatus can be obtained.

BRIEF DESCRIPTION OF THE DRAWINGS

The foregoing and further objects, features and advantages of the invention will become apparent from the following description of preferred embodiments with reference to the accompanying drawings, wherein like numerals are used to represent like elements and wherein.

DETAILED DESCRIPTION OF THE PREFERRED EMBODIMENTS

Hereinafter, best modes for carrying out the invention will be described with reference to the drawings.

A spot weld fracture analysis apparatus in accordance with the embodiment of the invention is realized by a computer (including a supercomputer) in which software that realizes a spot weld fracture analysis method described in detail below is incorporated. This software may be developed as an entirely novel group of software, but can also be created on the basis of an existing analysis software set (e.g., LS-DYNA, PAM-CRASH (both are registered trademarks in Japan), etc.). Or, it may also be developed as a software set that cooperates with an existing analysis software set, such as LS-DYNA, PAM-CRASH, etc., and provides additional functions.

A computer terminal that a user directly utilizes has, as user interfaces, for example, a mouse and a keyboard, and has a display that displays models for analysis, analysis results, etc. Besides, this computer terminal may be connected to, for example, a supercomputer that executes calculations of large loads, a CAD terminal that supplies CAD data that serves as a basis for an analysis model, etc., via an intra-company LAN or the like. Besides, in the computer terminal, a model creating software set (e.g., IDEAS, Hyper-Mesh (both are registered trademarks), etc.) may be installed.

The spot weld fracture analysis method according to the embodiment of the invention is executed in an analysis stage that comes after a model creating stage that is a prerequisite for the method. Incidentally, in accordance with analysis results obtained in the analysis stage or the like, modification of the model or the like is appropriately performed. Firstly, the model creating stage will be described.

In the model creating stage, a finite element model (CAE analysis model) of a structure article, that is, an analysis object, is created through the use of a model creating software set. The structure article that becomes an analysis object is arbitrary, for example, a body structure of a vehicle, a door unit thereof, etc. The finite element model is generally created on the basis of CAD data of such a structure article. Incidentally, since the embodiment of the invention, as described in detail below, relates to a fracture analysis of spot weld portions of three or more mutually superimposed plates that are spot-welded at a common welding point, any modeling technique may be selected for other portions as long as it is appropriate.

Figure 1A:
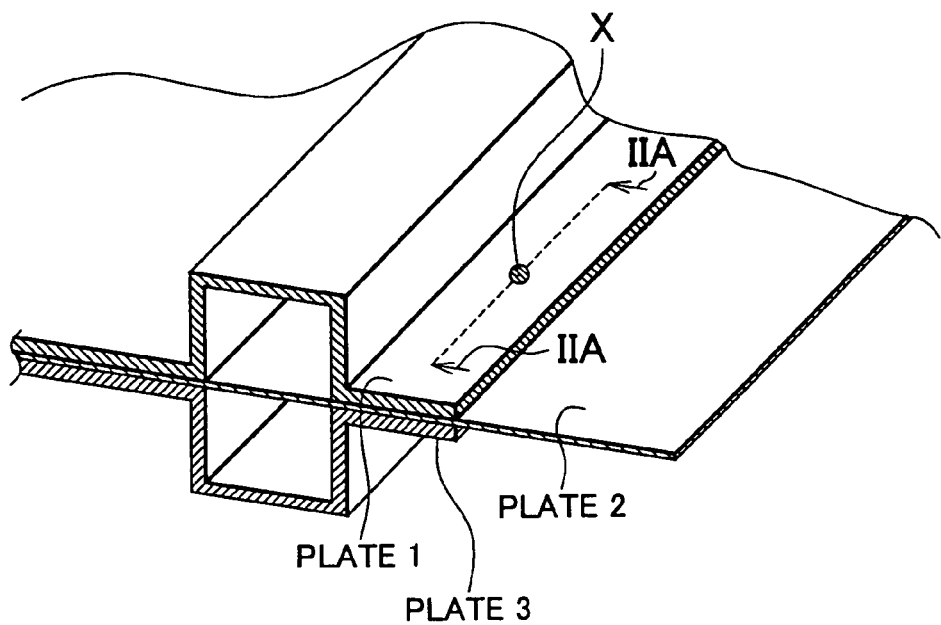
FIG. 1A is a perspective view showing a spot weld portion of three or more mutually superimposed plates that are spot-welded at a common welding point.
Figure 1B:
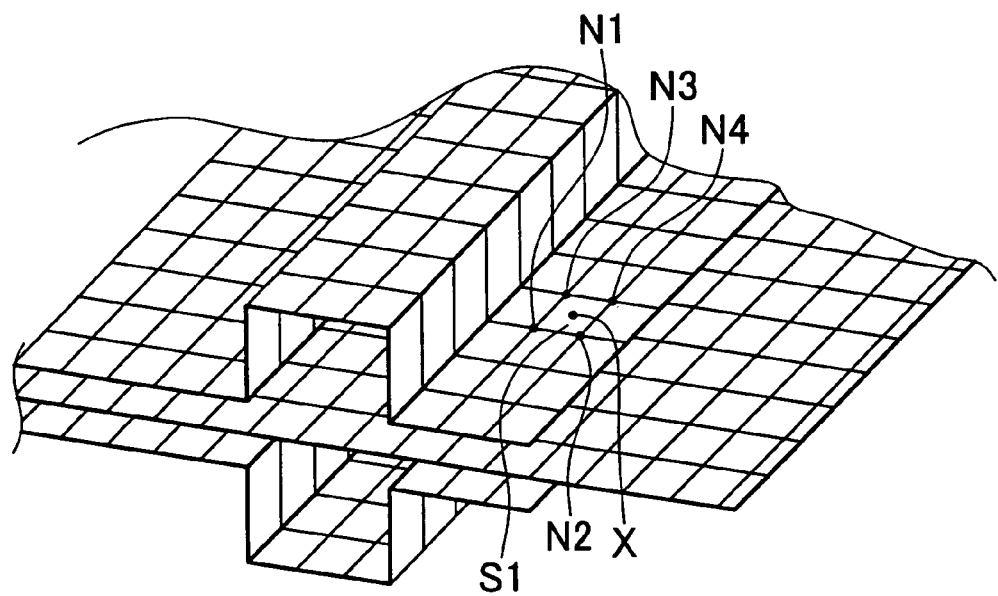
FIG. 1B is a perspective view showing an example of a finite element model thereof.

FIG. 1A shows a spot weld portion of three or more mutually superimposed plates that are spot-welded at a common welding point, the spot weld portion forming a portion of a structure article that becomes an analysis object. In FIGS. 1A and 1B, three plates 1, 2, 3 are spot-welded at a spot welding point position X, in a three-layer form. Hereinafter, the design-base plate thicknesses of the plates 1, 2, 3 are t1, t2, t3 [mm].

FIG. 1B is a perspective view showing an example of the finite element model of a portion including the spot weld portion which is shown in FIG. 1A. Each of the plates 1, 2, 3 is modeled by shell elements (plate elements). That is, surfaces of each plate 1, 2, 3 are mesh-divided by shell elements. The material property information of each shell element that is input includes the plate thickness t1, t2, t3 of the plate 1, 2, 3, the elasticity coefficient, the Poisson's ratio ν, the coefficient C (described later), etc., corresponding to the material of the plate 1, 2, 3. Incidentally, hereinafter, the shell elements corresponding to the spot welding point position X of the plates 1, 2, 3 will be referred to as "shell elements S1, S2, S3". Incidentally, in FIG. 1B, the shell elements S2, S3 of the plates 2, 3 are invisible behind shell elements of the plate 1.

Figure 2A:
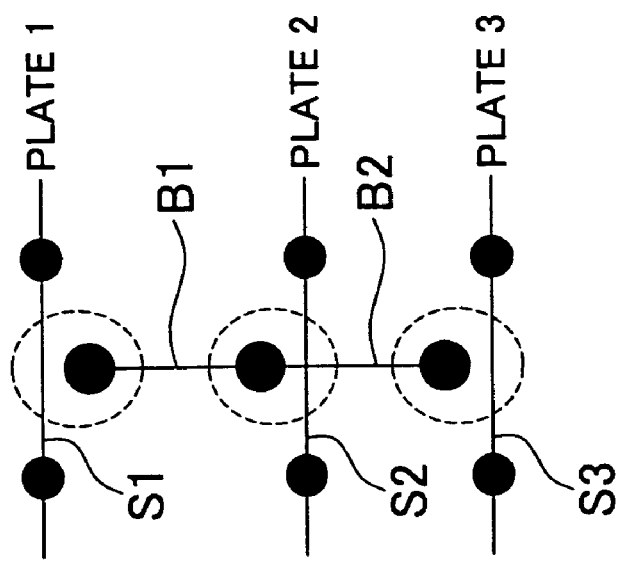
FIG. 2A schematically shows a section taken along line II-II in FIG. 1A.
Figure 2B:
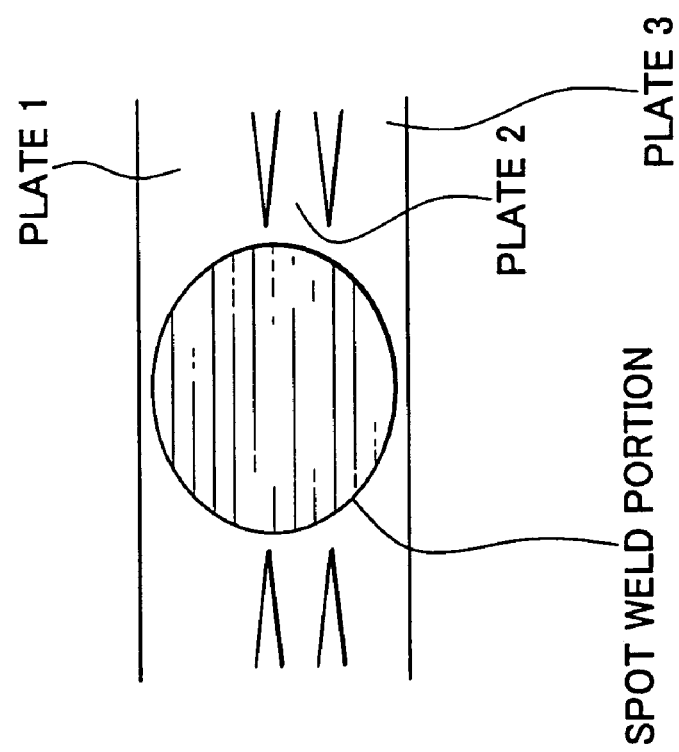
FIG. 2B is a sectional view schematically showing a section of a finite element model of a spot weld portion.

FIG. 2A schematically shows a section taken along line IIA-IIA in FIG. 1, and FIG. 2B schematically shows a section of a finite element model of the spot weld portion. In FIG. 2B, of the nodes of each shell element S1, S2, S3, two nodes of each shell element are schematically shown. For example, the nodes on both sides of the shell element S1 shown in FIG. 2B are a node N1 (N2) and a node N3 (N4) of the shell element S1 shown in FIG. 1B.

Figure 3:
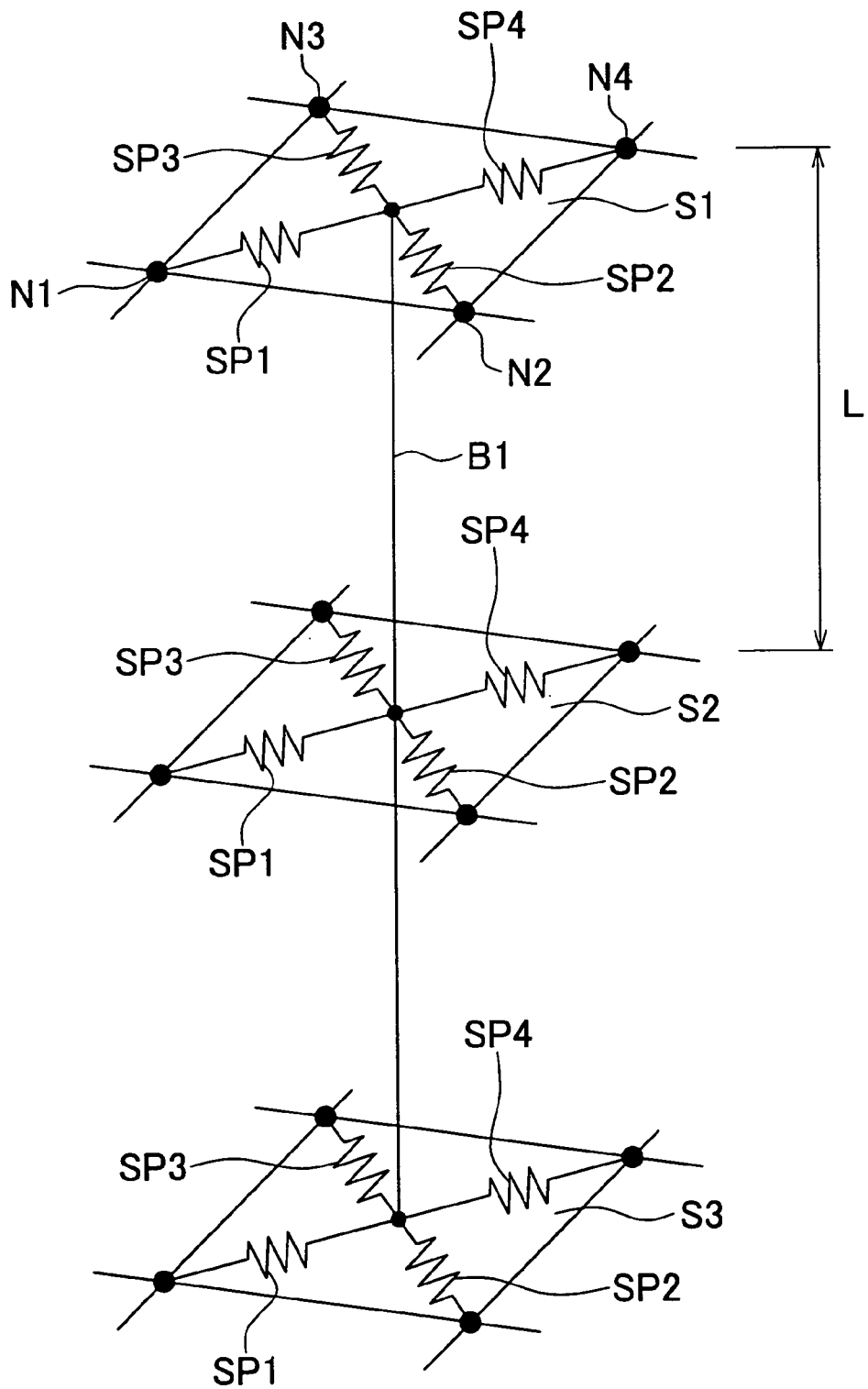
FIG. 3 is a perspective view showing an example of a finite element model in which the bonding between beam elements and shell elements is modeled.

As shown in FIG. 2B, the shell elements S1, S2, S3 corresponding to the spot welding point position of the three plates are interconnected via beam elements B1, B2. That is, the shell elements S1, S2 of the plates 1, 2 are interconnected via the beam element B1, and the shell elements S2, S3 of the plates 2, 3 are interconnected via the beam element B2. Each of the nodes of the beam elements B1, B2 is bonded to a connected-side one of the shell elements S1, S2, S3 (the bonds are shown by broken-line circular loops). This bonding may be modeled, for example, by connecting each node of a beam element (B1 or B2) and the four nodes of the connected-side shell element (S1, S2 or S3) (three nodes if the shell element is a triangular element) via special spring elements SP1 to SP4, as shown in FIG. 3. Incidentally, in FIG. 3, gaps L between the shell elements S1, S2, S3 are shown exaggeratedly enlarged for convenience of illustration of the finite element model.

The material property information of the beam elements B1, B2 (e.g., sectional shapes, various elasticity moduli thereof) and the material property information of the spring elements SP1 to SP4 (e.g., various elasticity moduli thereof) are appropriately set through the use of data from strength tests on actual spot weld portions and the like. In particular, the bonding between beam elements and shell elements may be modeled in any manner as long as appropriate binding relations are modeled between the nodes of the beam elements and the nodes of the shell elements.

Figure 4:
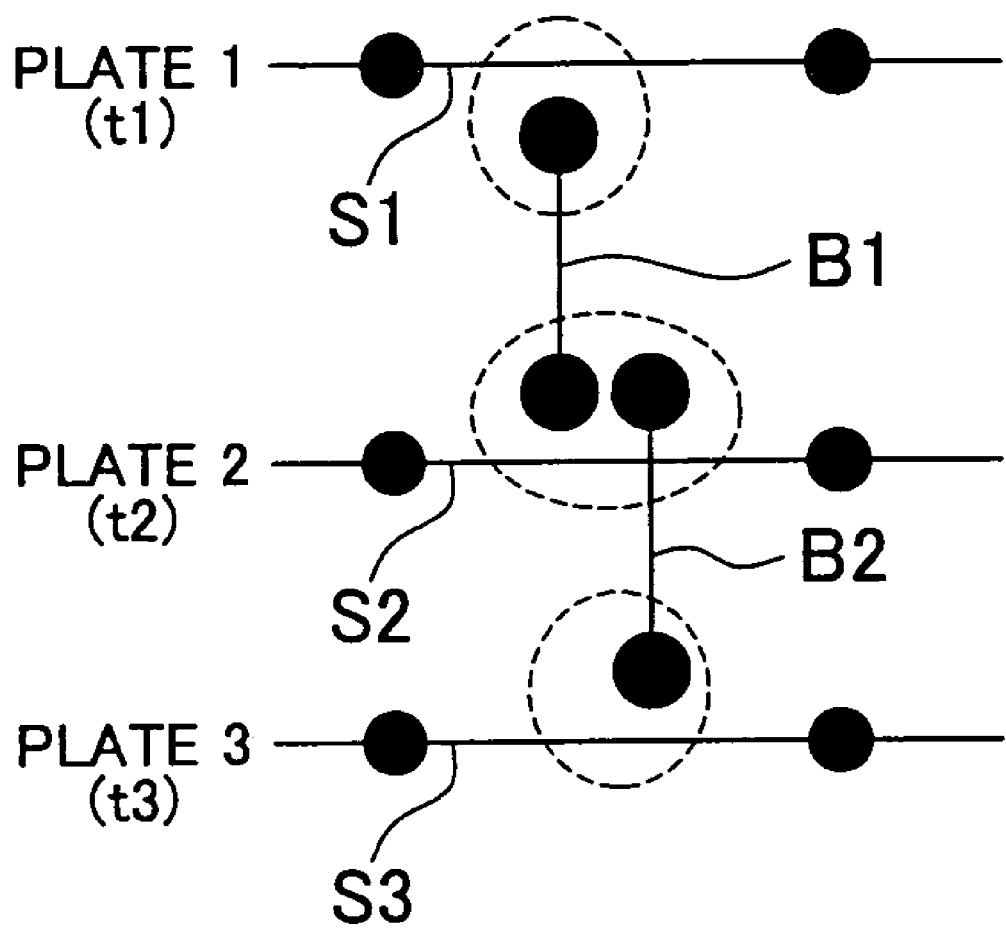
FIG. 4 is a sectional view schematically showing another embodiment of the finite element model of a spot weld portion.

FIG. 4 is a sectional view schematically showing another embodiment of the finite element model of a spot weld portion. In the example shown in FIG. 3, the beam elements B1, B2 share the node on the middle plate 2 side whereas, in the example shown in FIG. 4, the beam elements B1, B2 do not share a node on the middle plate 2 side. In this case, the two nodes of the beam elements B1, B2 on the plate 2 side are individually bonded to the shell element S2 in a manner as shown in FIG. 4. Thus, the beam elements B1, B2 may be directly interconnected as in the example of FIG. 3, or may also be in a relation of binding each other via the shell element S2 as in the example of FIG. 4.

Next, the analysis stage using the finite element model created as described above will be described. In the analysis stage in this embodiment, the possibility of fracture of a spot-weld portion, that is, fracture around a weld trace (nugget) on the plate, under an input load condition where a large force that may involve an impact acts on the spot weld portion of the plate is analyzed/predicted. Such analysis may be executed on a finite element model in which only a spot weld portion of the plate is locally modeled, in order to evaluate solely the spot weld portion of the plate. However, the analysis is particularly useful when used to evaluate whether there is a possibility of fracture in a spot-weld portion of a plate in an analysis-object structure article in a dynamic structural analysis and/or a nonlinear structural transition analysis using a finite element model of the entire structure article (typically, a collision analysis in which behaviors (deformation, impact value, etc.) of an entire vehicle at the time of a collision are simulated). For example, in the case of a vehicle, although there are thousands of spot weld portions, execution of a collision analysis using a finite element model of the entire vehicle makes it possible to evaluate in which spot weld portions and in which stages in the colliding process there is possibility of fracture, and to what extent the possibility of fracture is.

Figure 5:
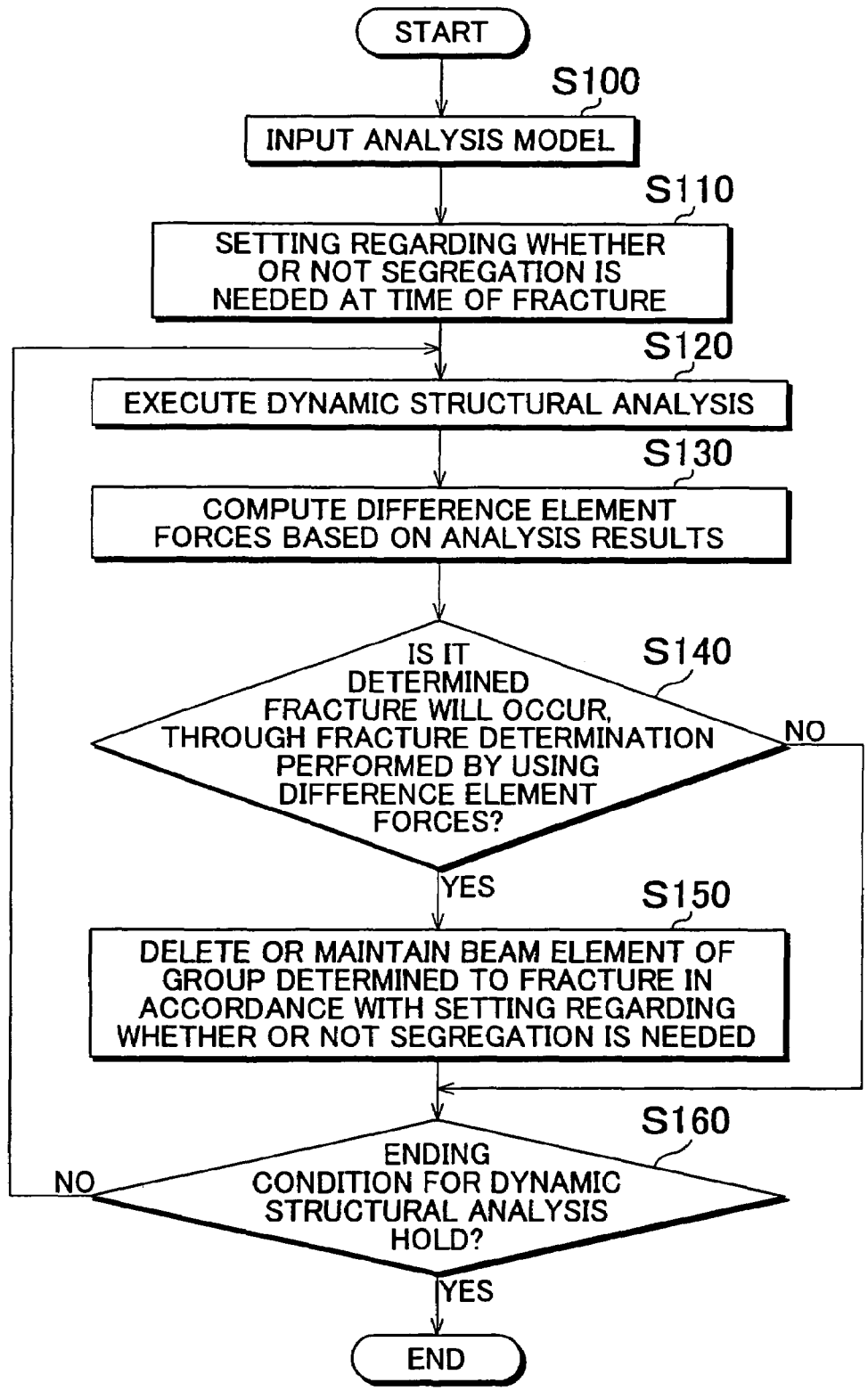
FIG. 5 is a flowchart showing a flow of a main process of a spot weld fracture analysis method according to an embodiment of the invention.

FIG. 5 is a flowchart showing the flow of a main process of a spot weld fracture analysis method according to the embodiment of the invention.

In step 100, a finite element model created as described above, and an input load condition are input as an analysis model. The input load condition may be a condition obtained by modeling, for example, a vehicle collision as mentioned above.

In step 110, how a spot weld portion that is determined to fracture is to be handled in a subsequent analysis (dynamic structural analysis) is set. In this embodiment, a user selects one of two handling methods: a handling method in which the spot weld portion that is determined to fracture is segregated, and a handling method in which the spot weld portion is left un-segregated. The handling methods will be described in detail later.

Figure 6:
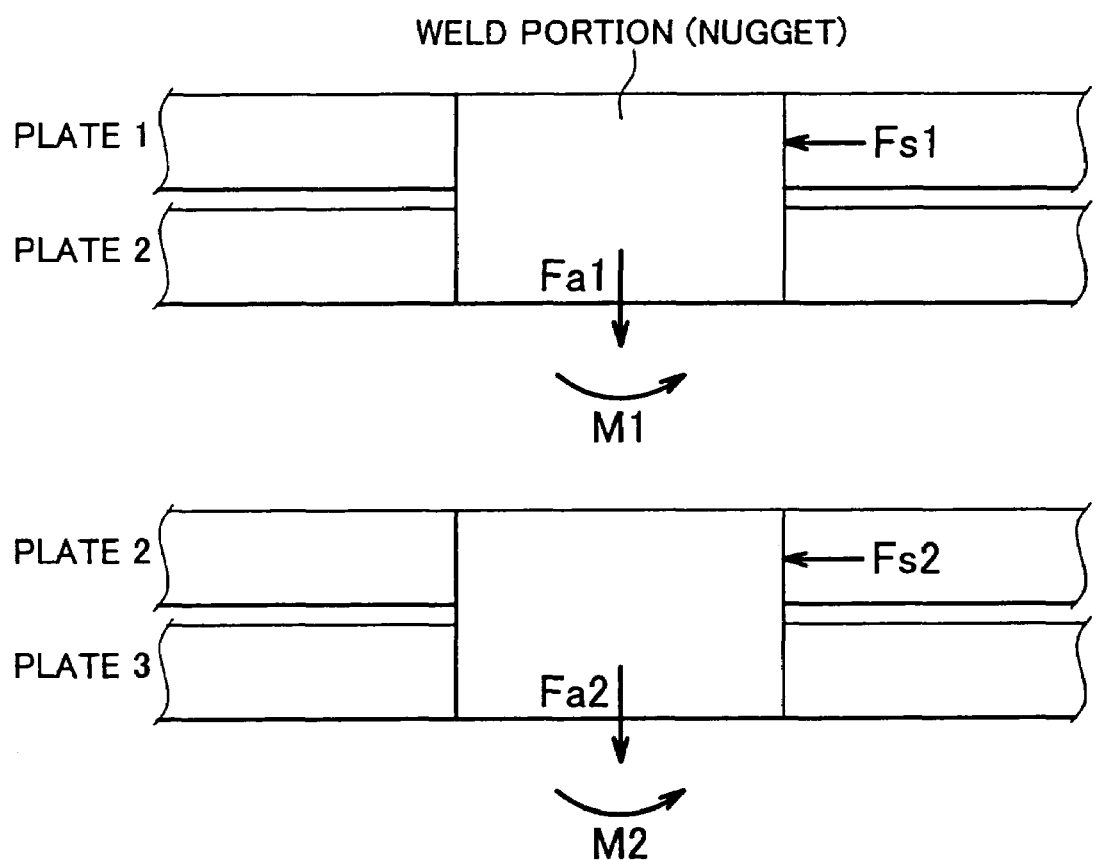
FIG. 6 is an explanatory diagram regarding element forces (Fa, Fs, M) of a beam element.

In step 120, the analysis is executed using the analysis model input in step 100. Hereinafter, the analysis in step 120 will also be referred to as "dynamic structural analysis". When this dynamic structural analysis is executed, time-series analysis results are output in every predetermined computation cycle. Incidentally, for example, in a collision analysis using a large-scale finite element model, computation is executed in a huge number of computation cycles. The analysis results can include diverse analytic values of parameters in accordance with the analysis-purpose; for example, the shell element strain $\epsilon$, the strain rate $d\epsilon/dt$, and the element force (force F, moment M) transferred to a shell element via a beam element are included. Incidentally, the strain $\epsilon$ is an equivalent plastic strain. With regard to the element force transferred to a shell element via a beam element (hereinafter, simply referred to as "element force of the beam element"), the force F includes the axial force Fa in the direction of an axis of the beam element, and the shearing force Fs, and the moment M includes the bending moment applied to the beam element. These element forces (Fa, Fs, M) of beam elements correspond to the axial force Fa, the shearing force Fs, and the bending moment M that act on each spot weld portion between two plates, as schematically shown in FIG. 6. Incidentally, in FIG. 6, the numerals suffixed to the symbols Fa, Fs, M correspond to the numbers of groups (beam elements).

In step 130, on the basis of the analysis results obtained in step 120, information regarding the element forces that act on each shell element (hereinafter, referred to as "beam element information") is generated separately for each one of groups which each are a combination of two adjacent plates of the three plates 1, 2, 3. In this example, since three plates 1, 2, 3 are provided, there are two groups, that is, a group of the middle plate 2 and the outside plate 1, and a group of the middle plate 2 and the inside plate 3. For each group, element force information is generated. At this time, the element forces of the beam elements B1, B2 that act on the shell element S2 of the middle plate 2 of the three plates 1, 2, 3 are found from a difference between the element forces of the two beam elements B1, B2 that are connected to the shell element S2.

Concretely, with regard to the first group of the middle plate 2 and the outside plate 1, the element force information about the shell element S1 is the element forces (Fa1, Fs1, M1) of the beam element B1 based on analysis results, while the element force information about the shell element S2 is the element forces (Fa1-Fa2, Fs1-Fs2, M1-M2) obtained by finding differences between the element forces of the beam elements B1, B2 based on analysis results, which hereinafter will be referred to as "difference element forces F'". Likewise, the element force information about the shell element S3 is the element forces (Fa2, Fs2, M2) of the beam element B2 based on analysis results, while the element force information about the shell element S2 is the difference element forces F' (Fa2-Fa1, Fs2-Fs1, M2-M1) between the element forces of the beam elements B2, B1 based on analysis results.

In step 140, the possibility of fracture of the spot weld portion is analyzed/predicted on the basis of the analysis results obtained in step 120 and the element force information obtained in step 130. Hereinafter, the analysis in step 140 will also be referred to as "fracture analysis".

Figure 7:
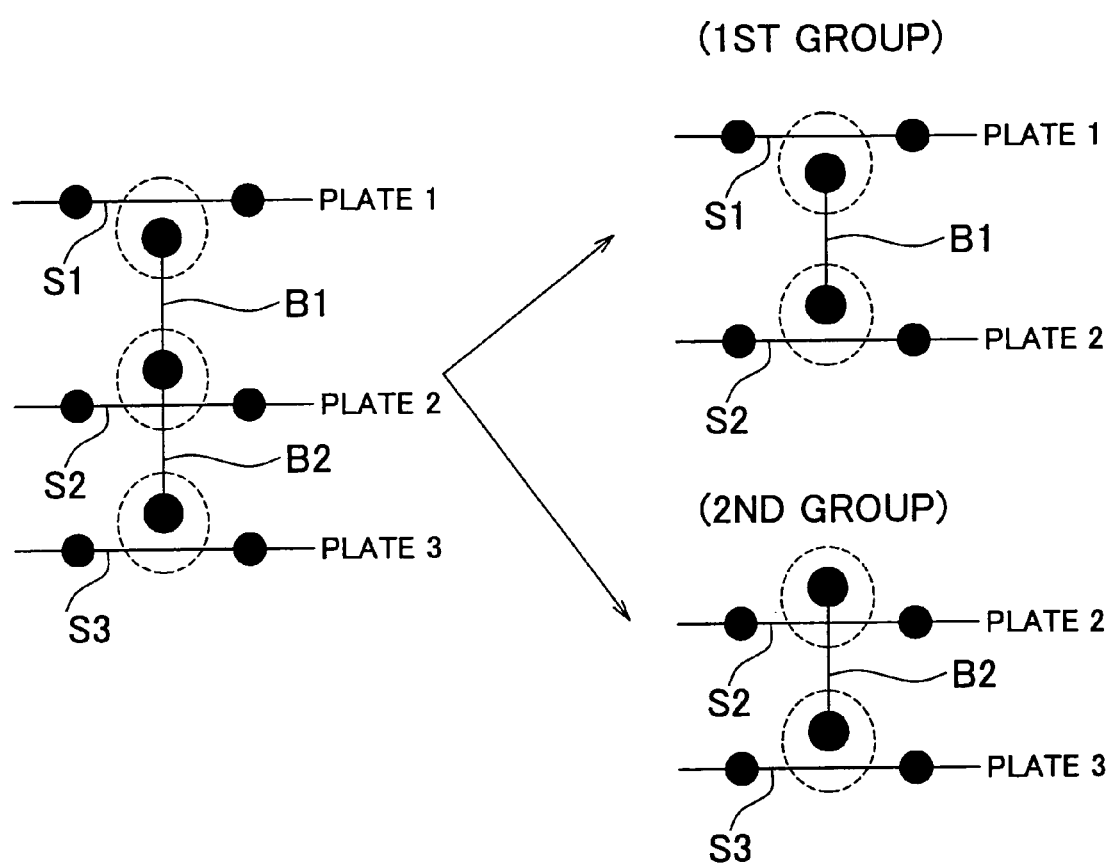
FIG. 7 is a diagram showing a finite element model of a spot weld portion in which three plates are welded at the same welding point, and a grouping manner.

In this embodiment, as schematically shown in FIG. 7, of the three plates 1, 2, 3, groups of plates are each formed of a combination of two adjacent plates, as mentioned above. In step 140, separately for each group, the possibility of fracture of the spot weld between the two plates of the group is analyzed/predicted. In this example, since three plates 1, 2, 3 are provided, there are two groups, that is, a group of the middle plate 2 and the outside plate 1, and a group of the middle plate 2 and the inside plate 3. The fracture analysis of the spot weld between the two plates is carried out in manners independent of each other in the two groups.

Concretely, a fracture function F (t, F, M, $\epsilon$, d$\epsilon$/dt, C) into which the plate thickness information of a shell element (plate thickness t of the plate), the element forces F, M of the beam element, the strains $\epsilon$ and the strain rate d$\epsilon$/dt of the shell element connected to the beam element, the coefficient C dependent on the material property are input as input parameters (variants), and which outputs an index value that presents the possibility of fracture regarding the shell element is used for the analysis/prediction. Into the fracture function F, known plate thickness information of a shell element (plate thickness t of the plate), analytic values (F, M, $\epsilon$, d$\epsilon$/dt)

obtained on the basis of analysis results of the dynamic structural analysis are input as input parameters. On the basis of a result of comparison between the then output value of the fracture function F and a given reference value Fcr (fracture criterion value Fcr), the possibility of fracture is analyzed/predicted. In each group, fracture of the spot weld between the two plates can occur separately on the individual plate sides. Therefore, the fracture function F is applied separately to the individual plates of each group (i.e., in each group, a total of two output values of the fracture function F are obtained on the two plate sides).

As for the analysis/prediction of the possibility of fracture based on an output value of the fracture function F, it may be determined, in principle, that fracture of the spot weld between the two plates of the concerned group will occur, if the output value of the fracture function F exceeds the fracture criterion value Fcr. In this case, the possibility of fracture is evaluated as either 0% of 100%. However, it is also possible to linearly evaluate the possibility of fracture, for example, by defining as a load factor the ratio of the output value of the fracture function F to the fracture criterion value Fcr.

Herein, as for the fracture function F (the coefficient C and the fracture criterion value Fcr), a fracture function adapted to fracture test results of the spot weld portion of the two plates through regression or the like is used (an example of the fracture function F will be described later). This is because with respect to a spot weld portion of three or more plates, the fracture evaluation technique established for a spot weld portion of two plates can also be applied, by performing the fracture analysis separately for each group as described above (in this case, there is no need to newly accumulate test data and adapt the fracture function F and the fracture criterion value Fcr to the spot weld portion of three or more plates).

However, if the fracture function F adapted to fracture test results of a two-plate spot weld portion is directly applied for the fracture analysis with respect to a spot weld portion of three or more plates, the fracture analysis regarding the middle plate 2 cannot be appropriately performed. This is explained as follows. The fracture function F is applied to the middle plate 2 as if the element forces (force F, moment M) of each one of the two beam elements B1, B2 act independently of each other. In reality, however, the individual element forces of the two beam elements B1, B2 rule the fracture phenomenon of the middle plate 2 while affecting each other.

Figure 8:
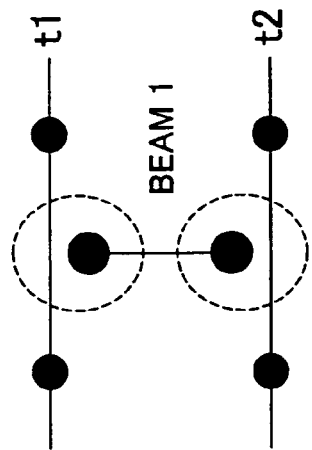
FIG. 8 is an explanatory diagram schematically showing a manner of fracture determination in which a fracture function F with respect to each plate of each group is used in a spot weld fracture analysis method according to the embodiment of the invention.
Figure 8:
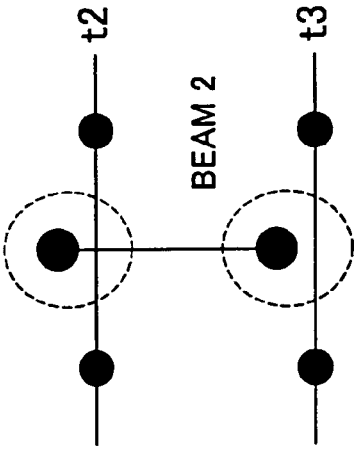

Therefore, in this embodiment, as schematically shown in FIG. 8, when the fracture function F is applied to the fracture analysis with respect to a spot weld portion of three or more plates, the beam element information obtained in step 130 is used to evaluate the possibility of fracture of the spot weld portion between the concerned two plates. Thus, with respect to the middle plate 2, the aforementioned difference element forces F' are used as element forces F of the beam element that are parameters to be input to the fracture function F. Incidentally, in FIG. 8, the numerals suffixed to the symbols t, $\epsilon$, dotted $\epsilon$ (=d$\epsilon$/dt), C correspond to the numbers of the plates.

Thus, in this embodiment, the possibility of fracture of the spot weld between the two plates of a group is evaluated as follows. With regard to the one (plate 2 in this embodiment) of the plates of the group which is connected to a plate of another group via a beam element, the element forces transferred to the shell element of the another group via the beam element of the another group are subtracted. Therefore, the fracture analysis taking into account the shares of element forces of groups becomes possible. Therefore, even in the fracture analysis of a spot weld portion of three or more plates, it is possible to maintain high analysis accuracy while utilizing the fracture evaluation technique established for the two-plate spot weld portion.

In more detail, for example, as shown in FIG. 6, in the case where the individual element forces (forces F1, F2, moments M1, M2) of two beam elements B1, B2 act on the middle plate 2, the possibility of fracture in the middle plate 2 should be smaller than in the case where the element forces act on the middle plate 2 independently of each other. This is because, of the element forces of the beam elements that act on the middle plate 2, the element forces from the beam element on one side are transferred via the beam element on the other side to the shell element of another group as well. If, despite that, the fracture function F is directly applied to the fracture analysis with respect to a spot weld portion of three or more plates, the possibility of fracture of the spot weld portion on the middle plate 2 side will be evaluated while taking into account only the element forces from the beam element on one side. Therefore, the possibility will be evaluated falsely as being high. Consequently, if this evaluation result regarding the middle plate 2 side is directly adopted, accuracy deterioration of the fracture analysis will be brought about.

In this embodiment, however, with respect to the middle plate 2, the individual element forces (F1, F2, M1, M2) of the beam elements B1, B2 are not used, but the difference element forces (F') therebetween are used, so that it becomes possible to perform a fracture analysis in which compensation is made for an actual phenomenon in which the element forces of the beam element of one group are transferred via the beam element of another group to the shell element of the another group as well. Therefore, it is possible to maintain high analysis accuracy even in the fracture analysis of a spot weld portion of three or more plates.

Referring to FIG. 5, if after the possibility of fracture of the spot weld portion is analyzed/predicted it is determined that fracture of the spot weld between the plates of a group will occur, the process proceeds to step 150. For example, it is determined whether or not the output value obtained by inputting the plate thickness information t2, the strain $\epsilon$2, the difference element forces F' (Fa2-Fa1, Fs2-Fs1, M2-M1), etc. of the shell element S2 of the middle plate 2 into the fracture function F has exceeded the fracture criterion value Fcr, or whether the output value obtained by inputting the plate thickness information t1 and the strain $\epsilon$1 of the shell element S1 of the outside plate 1, and the element forces (force F1, moment M1) of the beam element B1, etc. into the fracture function F has exceeded the fracture criterion value Fcr, it is determined that fracture of the spot weld portion will occur between the middle plate 2 and the outside plate 1. Then, the process proceeds to step 150.

In step 150, the spot weld portion that has been determined to fracture is segregated, or is maintained without being segregated, in accordance with the handling method selected in step 110.

Concretely, if the handling method in which the spot weld portion is to be segregated has been selected, the spot weld portion is segregated, and the analysis model is updated. At this time, the segregation of the spot weld portion of the three plates is realized, for example, by deleting only the beam element of the group that has been determined to fracture. In this case, from the next computation cycle on, the dynamic structural analysis in step 130 is executed with an analysis model in which the aforementioned beam element is not present. For example, if the fracture analysis of the first group of the middle plate 2 and the outside plate 1 results in a determination that fracture will occur in the spot weld between the two plates, only the beam element B1 is deleted.

After that, using an analysis model in which only the spot weld between the shell element S2 of the middle plate 2 and the shell element S3 of the inside plate 3 is effective, the dynamic structural analysis in step 130 is continued. Therefore, it is possible to analyze not only the possibility of fracture of a spot weld but also the behavior of the structure article after the spot weld fractures (influences caused by the fracture).

On the other hand, if the handling method in which the spot weld portion is not to be segregated has been selected, the process proceeds to step 160 without deleting the beam element. Such a handling method is useful, for example, in the dynamic structural analysis of the structure article in which the fracture of a spot weld is not allowable, and is also useful in that destabilization of the dynamic structural analysis can be prevented. In a structure article in which fracture of a spot weld is not allowable, if it is determined that a spot weld will fracture, a countermeasure is taken, for example, addition of a new spot weld around the determined-to-fracture spot weld, or the like. Then, the dynamic structural analysis and the fracture analysis are executed again by using an analysis model in which the aforementioned counter measure has been modeled.

Incidentally, in the case where the entire vehicle is the analysis-object structure article, there are a plurality of spot weld portions. In this case, a construction may be provided such that a handling method that is used after determination of fracture of a spot weld portion can be set separately for each spot weld portion.

In step 160, an ending condition for the dynamic structural analysis executed in step 130 is checked. This ending condition is appropriately set. For example, if a collision analysis is performed as a dynamic structural analysis, the ending condition may be the stage where the collision of the vehicle ends. Unless the ending condition for the dynamic structural analysis is satisfied, the process returns to step 120, in which the dynamic structural analysis in the next computation cycle is executed, which is subsequently repeatedly executed in a like fashion. Incidentally, the fracture analysis in step 140 may be executed in every computation cycle of the dynamic structural analysis, through the use of analysis results of the dynamic structural analysis that are output in the same computation cycles, or may also be executed in every cycle that is longer than the computation cycle of the dynamic structural analysis, through the use of analysis results of the dynamic structural analysis that are output in the same increased cycles.

As described above, according to the embodiment, one of the two shell elements of each group which also belongs to another group is subjected to the fracture analysis with an extra plate thickness added in, through the use of analysis results of the dynamic structural analysis. Therefore, high analysis accuracy can be maintained even in the fracture analysis of a spot weld portion of three or more plates.

Next, an example of the fracture function F (fracture determination method) used in the foregoing embodiment will be described.

The fracture determination method is defined by the following determination expression on the basis of the maximum shearing stress $\tau$ around a spot weld portion (nugget) caused by the axial force Fa and the moment M of the beam element, and the maximum tension stress $\sigma$ of the spot weld portion (nugget) caused by the shearing force Fs of the beam element.

$$\left(\frac{\tau}{\tau^F(\dot{\varepsilon})}\right)^2 + \left(\frac{\sigma}{\sigma^F(\dot{\varepsilon})}\right)^2 \geq 1 \quad (1)$$

Herein, $\tau = Fa/(2\pi \cdot t \cdot r) + M/(\alpha \cdot t \cdot r^2)$, $\sigma = Fs/(\frac{1}{2}\pi \cdot t \cdot r)$ where t is the plate thickness information, and r is the nugget radius (known). The coefficient $\alpha$ is a value that depends on the elastoplastic property (property between being elastic and being entirely plastic) of a shell element (plate), and is included in the coefficient C that is a parameter of the fracture function F.

Besides, $\sigma^F$ and $\tau^F$ in the denominator on the left-hand side represent critical stresses, and both are functions dependent on the strain rate $d\varepsilon/dt$. As for an example, $\sigma^F$ and $\tau^F$ are defined as follows, by using the Cooper-Simmons expression.

$$\sigma^F(\dot{\varepsilon}) = \sigma^F_{(c=p=o)}\left[1 + \left(\frac{\dot{\varepsilon}}{c}\right)^{1/p}\right] \quad (2)$$

$$\tau^F(\dot{\varepsilon}) = \tau^F_{(c=p=o)}\left[1 + \left(\frac{\dot{\varepsilon}}{c}\right)^{1/p}\right]$$

In the expressions, $\sigma^F_{(c=p=0)}$ and $\tau^F_{(c=p=0)}$ represent the critical stresses of a shell element (plate) when there is no strain dependency, and c and p are coefficients determined by the material property of the shell element (plate), and is included in the coefficient C that is a parameter of the fracture function F.

In this example, the fracture criterion value Fcr is 1. In other words, the fracture criterion value Fcr is group at 1, and the coefficients are adapted.

In this case, when in the first group of the middle plate 2 and the outside plate 1, the possibility of fracture on the middle plate 2 side is to be evaluated, the difference element forces F' (Fa1-Fa2, Fs1-Fs2, M1-M2) are input as element forces (Fa, Fs, M) to the fracture function F, and at the same time, the strain rate $d\varepsilon/dt$ of the shell element S2 (that is a derivative value of the strain $\varepsilon 2$ obtained by dividing the difference between the previous value and the present value of the strain $\varepsilon 2$ by the one computation cycle period, which is applied likewise hereinafter), the plate thickness information t2 thereof and the coefficient C2 ($\alpha 2$, c2, p2) are input to the fracture function F. When the possibility of fracture on the outside plate 1 side in the first group is to be evaluated, the element forces (Fa1, Fs1, M1) of the beam element B1 are input as element forces (Fa, Fs, M) to the fracture function F, and the strain rate $d\varepsilon/dt$ (derivative value of the strain $\varepsilon 1$) and the plate thickness information t1 of the shell element S1 and the coefficient C1 ($\alpha 1$, c1, p1) are input to the fracture function F. Then, in the embodiment, on the basis of the relation between the greater one of the two output values of the fracture functions F and the fracture criterion value Fcr, the possibility of fracture of the spot weld between the middle plate 2 and the outside plate 1 is evaluated as described above.

Likewise, when in the second group of the middle plate 2 and the inside plate 3, the possibility of fracture on the middle plate 2 side is to be evaluated, the difference element forces F' (Fa2-Fa1, Fs2-Fs1, M2-M1) are input as element forces (Fa, Fs, M) to the fracture function F, and at the same time, the strain rate $d\varepsilon/dt$, the plate thickness information t2 and the coefficient C2 of the shell element S2 are input to the fracture function F. When the possibility of fracture on the inside plate 3 side in the second group is to be evaluated, the element forces (Fa2, Fs2, Ms) of the beam element B2 are input as element forces (Fa, Fs, M) of the beam element B2 are input to the fracture function F, and at the same time, the strain rate d$\epsilon$/dt (derivative value of the strain $\epsilon$3), the plate thickness information t3 and the coefficient C3 ($\alpha$3, c3, p3) of the shell element S3 are input to the fracture function F. Then, in the embodiment, on the basis of the relation between the greater one of the two output values of the fracture functions F and the fracture criterion value Fcr, the possibility of fracture of the spot weld between the middle plate 2 and the inside plate 3 is evaluated.

While the preferred embodiments of the invention have been described in detail above, the invention is not restricted by the foregoing embodiments, but various modifications and replacements may be made in the foregoing embodiments without departing from the scope of the invention.

For example, although in the foregoing embodiments, the dynamic structural analysis and the fracture analysis are executed in a simultaneous parallel fashion, it is also possible to execute the fracture analysis as a post-process by using analysis results of the dynamic structural analysis.

Furthermore, in the foregoing embodiments, the coefficient C regarding a certain plate may change in accordance with the material property of the other plate in the group that includes the concerned plate. For example, when in the second group of the middle plate 2 and the inside plate 3, the possibility of fracture on the middle plate 2 side is to be evaluated, a coefficient C3 that depends on the material property of the plate 3 as well as the aforementioned various parameters may be input to the fracture function F.

Figure 9:
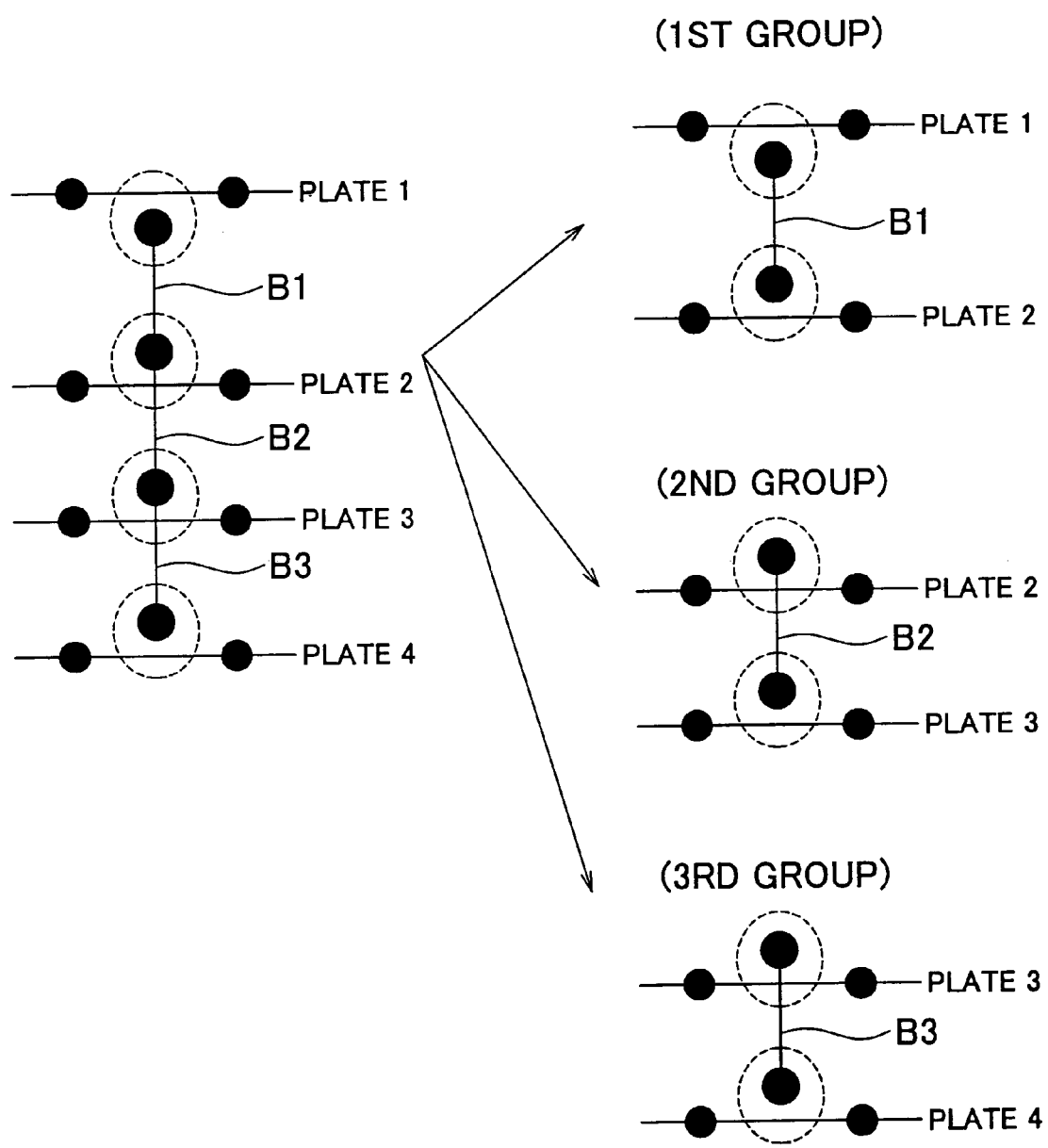
FIG. 9 is a diagram showing a finite element model of a spot weld portion in which four plates are welded at the same welding point, and a grouping manner.

Furthermore, the foregoing embodiments, as representative examples, relate to a spot weld of three plates. However, as shown in FIG. 9, with respect to a spot weld portion where four plates 1, 2, 3, 4 are welded at the same welding point, too, the possibility of fracture of a spot weld portion between two plates can also be evaluated separately for each group in substantially the same manners as described above, by forming three groups of two plates. In this case, the element force information of the middle plate 2 relevant to the first group is difference element forces F' (Fa1-Fa2, Fs1-Fs2, M1-M2), and the element force information of the middle plate 2 relevant to the second group is difference element forces F' (Fa2-Fa1, Fs2-Fs1, M2-M1), and the element force information of the middle plate 3 relevant to the second group is difference element forces F' (Fa2-Fa3, Fs2-Fs3, M2-M3), and the element force information of the middle plate 3 relevant to the third group is difference element forces F' (Fa3-Fa2, Fs3-Fs2, M3-M2). In addition, in the invention, in the case where more than three plates are spot-welded, a middle plate refers to a plate that is sandwiched by other plates.

What is claimed is:

1. A spot weld fracture analysis method implemented by a fracture analysis apparatus for a spot weld portion of three or more mutually superimposed plates that are spot-welded at a common welding point, comprising:
   modeling an upper plate, a lower plate, and every plate disposed therebetween by shell elements;
   executing an analysis under a predetermined input load condition by using a finite element model in which shell elements corresponding to a spot weld point position of each plate of the three or more plates are individually interconnected via beam elements;
   finding, using the fracture analysis apparatus, an element force of a beam element that acts on a shell element relevant to every plate disposed between the upper plate and the lower plate from a difference between the element forces of two beam elements that are connected to the shell element relevant to every plate disposed between the upper plate and the lower plate on a basis of an analysis result obtained via the analysis; and
   predicting a possibility of fracture of a spot weld between at least one plate disposed between the upper plate and the lower plate and an adjacent plate based on the element force found.

2. The spot weld fracture analysis method implemented by a fracture analysis apparatus according to claim 1, further comprising:
   using, in order to predict the possibility of fracture of the spot weld, a given fracture function that, through inputting as parameters at least an element force of a beam element, a strain of a shell element connected to the beam element, and plate thickness information regarding a plate relevant to the shell element, outputs an index value that represents a possibility of fracture on a side of the plate relevant to the shell element;
   judging, using the fracture analysis apparatus, the possibility of fracture of the spot weld between the middle plate and the adjacent plate on a basis of an output value of the fracture function relevant to each plate; and
   inputting the difference element force as an element force of the beam element that is one of the parameters, into the fracture function relevant to the at least one plate disposed between the upper plate and the lower plate.

3. A computer-readable storage encoded with a computer program, wherein the program, when executed by a processor, causes the processor to perform a method comprising:
   modeling an upper plate, a lower plate, and every plate disposed therebetween by shell elements;
   executing an analysis under a predetermined input load condition by using a finite element model in which shell elements corresponding to a spot weld point position of each plate of the three or more plates are individually interconnected via beam elements;
   finding an element force of a beam element that acts on a shell element relevant to every plate disposed between the upper plate and the lower plate from a difference between the element forces of two beam elements that are connected to the shell element relevant to every plate disposed between the upper plate and the lower plate on a basis of an analysis result obtained via the analysis; and
   predicting a possibility of fracture of a spot weld between at least one plate disposed between the upper plate and the lower plate and an adjacent plate based on the element force found.

4. A spot weld fracture analysis apparatus for a spot weld portion of three or more mutually superimposed plates that are spot-welded at a common welding point, comprising:
   a computer, wherein the computer comprises:
   a model creation device that models each an upper plate, a lower plate, and every plate disposed there between by shell elements;
   an analysis device that acquires an analysis result of a dynamic structural analysis based on a finite element model in which shell elements corresponding to a spot weld point position of each plate of the three or more plates are individually interconnected via beam elements; and
   a prediction device that finds an element force of a beam element that acts on a shell element relevant to at least one plate disposed between the upper plate and the lower plate from a difference between the element forces of two beam elements that are connected to the shell element relevant to the at least one plate disposed between the upper plate and the lower plate on a basis of the analysis result, and that predicts a possibility of fracture of a spot weld between the at least one plate disposed between the upper plate and the lower plate and an adjacent plate based on the difference element force found from the difference.

* * * * *

UNITED STATES PATENT AND TRADEMARK OFFICE
CERTIFICATE OF CORRECTION

PATENT NO. : 7,672,819 B2  Page 1 of 1
APPLICATION NO. : 11/580163
DATED : March 2, 2010
INVENTOR(S) : Kumagai It is certified that error appears in the above-identified patent and that said Letters Patent is hereby corrected as shown below:

On the title page, Item (73), the Assignee's information is incorrect. Item (73) should read:

-- (73) Assignee: Toyota Jidosha Kabushiki Kaisha,
Toyota-shi (JP) --

Signed and Sealed this

Twenty-seventh Day of April, 2010

David J. Kappos
*Director of the United States Patent and Trademark Office*